US012044634B2

(12) United States Patent
Gill et al.

(10) Patent No.: US 12,044,634 B2
(45) Date of Patent: Jul. 23, 2024

(54) X-RAY AUTOMATED CALIBRATION AND MONITORING

(71) Applicant: John Bean Technologies Corporation, Chicago, IL (US)

(72) Inventors: Jeffrey C. Gill, Stone Ridge, NY (US); Amer M. Butt, Williamsville, NY (US); Richard D. Timperio, Catskill, NY (US)

(73) Assignee: JOHN BEAN TECHNOLOGIES CORPORATION, Chicago, IL (US)

( * ) Notice: Subject to any disclaimer, the term of this patent is extended or adjusted under 35 U.S.C. 154(b) by 157 days.

(21) Appl. No.: 17/635,208

(22) PCT Filed: Aug. 13, 2020

(86) PCT No.: PCT/US2020/046178
§ 371 (c)(1),
(2) Date: Feb. 14, 2022

(87) PCT Pub. No.: WO2021/034610
PCT Pub. Date: Feb. 25, 2021

(65) Prior Publication Data
US 2022/0291148 A1 Sep. 15, 2022

Related U.S. Application Data

(60) Provisional application No. 62/888,209, filed on Aug. 16, 2019.

(51) Int. Cl.
*G01N 23/18* (2018.01)
*G01N 23/04* (2018.01)
(Continued)

(52) U.S. Cl.
CPC ............. *G01N 23/18* (2013.01); *G01N 23/04* (2013.01); *G01N 23/083* (2013.01); *G01N 33/02* (2013.01);
(Continued)

(58) Field of Classification Search
None
See application file for complete search history.

(56) References Cited

U.S. PATENT DOCUMENTS

| 7,356,115 B2 * | 4/2008 | Ford | G01V 5/005 |
| | | | 378/57 |
| 7,742,568 B2 * | 6/2010 | Smith | G01N 23/087 |
| | | | 378/57 |

(Continued)

FOREIGN PATENT DOCUMENTS

| CN | 1745296 A | 3/2006 |
| CN | 102056545 A | 5/2011 |

(Continued)

OTHER PUBLICATIONS

Office Action mailed Aug. 2, 2023, issued in Chinese Patent Application No. 202080057713.5, filed Aug. 13, 2020, 14 pages.

(Continued)

*Primary Examiner* — Thomas R Artman
(74) *Attorney, Agent, or Firm* — Christensen O'Connor Johnson Kindness PLLC

(57) ABSTRACT

A scanner comprises an electromagnetic wave source; a collimator positioned to alter the electromagnetic waves emitted from the electromagnetic wave source into an electromagnetic beam; and a detector positioned to measure one or more levels of electromagnetic energy of the electromagnetic beam, wherein a collimator element is spatially adjustable in at least one axis via one or more adjusting mecha- (Continued)

nisms to change the one or more levels of electromagnetic energy measured the detector.

18 Claims, 9 Drawing Sheets

(51) Int. Cl.
　　　*G01N 23/083*　　　(2018.01)
　　　*G01N 33/02*　　　(2006.01)
(52) U.S. Cl.
　　　CPC . *G01N 2223/04* (2013.01); *G01N 2223/1016* (2013.01); *G01N 2223/303* (2013.01); *G01N 2223/3035* (2013.01); *G01N 2223/306* (2013.01); *G01N 2223/316* (2013.01); *G01N 2223/3307* (2013.01); *G01N 2223/3308* (2013.01); *G01N 2223/50* (2013.01); *G01N 2223/5015* (2013.01); *G01N 2223/618* (2013.01); *G01N 2223/643* (2013.01); *G01N 2223/645* (2013.01); *G01N 2223/652* (2013.01)

(56) References Cited

U.S. PATENT DOCUMENTS

| | | | | |
|---|---|---|---|---|
| 7,957,506 B2* | 6/2011 | Smith | ............... | G01N 23/087 378/57 |
| 8,000,436 B2* | 8/2011 | Seppi | ............... | G01N 23/046 378/57 |
| 8,116,431 B2* | 2/2012 | Smith | ............... | G01V 5/0041 378/57 |
| 8,948,338 B2* | 2/2015 | Barbato | ............... | G01T 1/20185 250/370.11 |
| 8,989,348 B2* | 3/2015 | Cox | ............... | G01N 23/04 378/146 |
| 9,435,752 B2* | 9/2016 | Morton | ............... | G01N 23/04 |
| 9,883,840 B2* | 2/2018 | Barbato | ............... | A61B 6/4233 |
| 9,910,184 B2* | 3/2018 | Li | ............... | G01V 5/0016 |
| 2004/0109532 A1* | 6/2004 | Ford | ............... | G01N 23/046 378/57 |
| 2009/0067575 A1* | 3/2009 | Seppi | ............... | G01N 23/046 378/57 |
| 2009/0086907 A1 | 4/2009 | Smith | | |
| 2010/0177868 A1* | 7/2010 | Smith | ............... | G01V 5/0041 378/57 |
| 2011/0222733 A1* | 9/2011 | Smith | ............... | G01N 23/087 382/104 |
| 2013/0114789 A1* | 5/2013 | Barbato | ............... | A61B 6/4233 378/62 |
| 2013/0129043 A1 | 5/2013 | Morton et al. | | |
| 2013/0202087 A1 | 8/2013 | Cox | | |
| 2014/0192958 A1* | 7/2014 | Dinca | ............... | H01J 35/02 378/64 |
| 2015/0146854 A1* | 5/2015 | Barbato | ............... | G01T 1/20185 378/62 |
| 2016/0170074 A1* | 6/2016 | Li | ............... | G21K 1/02 378/57 |
| 2016/0260572 A1* | 9/2016 | Dinca | ............... | G01V 5/0016 |
| 2022/0291148 A1* | 9/2022 | Gill | ............... | G01N 23/04 |
| 2022/0317063 A1* | 10/2022 | Gill | ............... | G01N 23/18 |

FOREIGN PATENT DOCUMENTS

| | | |
|---|---|---|
| CN | 102822696 A | 12/2012 |
| CN | 104024888 A | 9/2014 |
| CN | 104903708 A | 9/2015 |
| EP | 3 373 045 A1 | 9/2018 |

OTHER PUBLICATIONS

International Search Report and Written Opinion mailed Feb. 5, 2021, issued in corresponding International Patent Application No. PCT/US2020/046178, filed Aug. 13, 2020, 21 pages.
Communication Under 94(3) mailed Dec. 2, 2022, issued in corresponding European Patent Application No. 20 761 701.0, filed Aug. 13, 2020, 6 pages.

\* cited by examiner

X-RAY AUTOMATED CALIBRATION AND MONITORING

BACKGROUND

Electromagnetic wave scanners are used in various industries to detect manufacturing defects or foreign bodies in machine parts and food items. Some scanners rely on a collimator to change the source of electromagnetic waves into a high aspect rectangular beam (fan beam) that is projected onto a moving conveyor belt carrying the items to be scanned. However, problems arise because the source of electromagnetic waves can drift from its original settings or the collimator or detector can shift spatially due to vibrations or continued use. Therefore, the detector cannot accurately detect the defects or foreign bodies. Accordingly, this disclosure addresses the adjustment of collimators and the electromagnetic wave source used in scanners.

SUMMARY

In one embodiment, a scanner comprises an electromagnetic wave source; a collimator positioned to alter the electromagnetic waves emitted from the electromagnetic wave source into an electromagnetic beam; and a detector positioned to measure one or more levels of electromagnetic energy of the electromagnetic beam, wherein a collimator element is spatially adjustable in at least one axis via one or more adjusting mechanisms to change the one or more levels of the electromagnetic energy measured the detector.

In one embodiment, the electromagnetic wave source generates X-rays.

In one embodiment, a footprint of the electromagnetic beam comprises a high aspect rectangular shape.

In one embodiment, a collimator shielding element is spatially adjustable to translate and rotate in at least one axis.

In one embodiment, a collimator shielding element is spatially adjustable to translate and rotate in three axes.

In one embodiment, the detector comprises a stack of photodiode arrays.

In one embodiment, the scanner comprises a conveyor belt juxtaposed between the collimator and the detector.

In one embodiment, the scanner comprises one or more manually adjustable adjusting mechanisms to spatially adjust a collimator shielding element without tools.

In one embodiment, the scanner comprises one or more adjusting mechanisms coupled to actuators to spatially adjust a collimator shielding element with control system components.

In one embodiment, the control system components include at least a storage medium and one or more central processing units configured to communicate with the actuators.

In one embodiment, the scanner comprises a human machine interface configured to communicate with the one or more central processing units.

In one embodiment, the scanner is configured to communicate with a storage medium having instructions stored thereon to perform a method for detecting misalignment of the collimator, the method comprising:
with the detector, measuring energy levels of the electromagnetic beam produced by the collimator;
with a control system, comparing energy levels of the electromagnetic beam measured by the detector to predetermined values of energy levels of an aligned collimator; and
spatially adjusting the collimator when a measured energy level measured by the detector is outside of a predetermined value.

In one embodiment, the scanner is configured to communicate with a storage medium having instructions stored thereon to perform a method for stepping through multiple combinations of parameters to gather data for balancing energy levels detected by a detector, the method comprising:
with a control system, operating the electromagnetic wave source to generate an electromagnetic beam at a plurality of combinations of parameters; with the control system, incrementally moving a step plate fixture having a plurality of steps to expose the electromagnetic beam to a plurality of steps;
with the control system, measuring one or more energy levels of the electromagnetic beam at more than one of steps and at more than one combination of parameters; and
with the control system, selecting the combination of parameters that balances the energy levels detected by the detector.

In one embodiment, a tangible computer readable medium is provided having instructions stored thereon to perform a method for detecting misalignment of a collimator, the method comprising, with a detector, measuring energy levels of an electromagnetic beam produced by the collimator; with a control system, comparing energy levels of the electromagnetic beam measured by the detector to predetermined values of energy levels of an aligned collimator; and spatially adjusting the collimator when a measured energy level measured by the detector is outside of a predetermined value.

In one embodiment, a tangible computer readable medium is provided having instructions stored thereon to perform a method for stepping through multiple combinations of parameters to gather data for balancing energy levels detected by a detector, the method comprising, with a control system, operating an electromagnetic wave source to generate an electromagnetic beam at a plurality of combinations of parameters; with the control system, incrementally moving a step plate fixture having a plurality of steps to expose the electromagnetic beam to a plurality of steps; with the control system, measuring one or more energy levels of the electromagnetic beam at more than one of steps and at more than one combination of parameters; and with the control system, selecting the combination of parameters that most balances or maximizes the energy levels detected by the detector.

In one embodiment, a method is provided for detecting misalignment of a collimator, the method comprising, with a detector, measuring energy levels of an electromagnetic beam produced by a collimator that alters electromagnetic waves produced by an electromagnetic wave source; with a control system, comparing energy levels of the electromagnetic beam measured by a detector to predetermined values of energy levels of an aligned collimator; spatially adjusting the collimator when a measured energy level measured by the detector is outside of a predetermined value; and providing feedback of the present energy levels when a spatial adjustment is made to the collimator.

In one embodiment, the method comprises inspecting items on a conveyor belt passing through the electromagnetic beam.

In one embodiment, the method comprises halting inspecting the items when a measured energy level is outside of a predetermined limit.

In one embodiment, the method comprises starting inspecting the items after the collimator has been spatially aligned.

In one embodiment, the method comprises spatially adjusting the collimator with one or more actuators under the control of the control system.

In one embodiment, the electromagnetic beam comprises a high aspect rectangular footprint.

In one embodiment, a method is provided for stepping through multiple combinations of parameters to gather data for balancing energy levels detected by a detector, the method comprising, with a control system, operating an electromagnetic wave source to generate an electromagnetic beam at a plurality of combinations of parameters; with the control system, incrementally moving a step plate fixture having a plurality of steps to expose the electromagnetic beam to a plurality of steps; with the control system, measuring one or more energy levels of the electromagnetic beam at more than one of steps and at more than one combination of parameters; and with the control system, selecting the combination of parameters that most balances or maximizes the energy levels detected by the detector.

In one embodiment, the electromagnetic beam comprises a high aspect rectangular footprint.

In one embodiment, the method comprises inspecting items on a conveyor belt passing through the electromagnetic beam.

In one embodiment, the most balanced energy levels comprises having the energy levels from both sides of the electromagnetic beam be most nearly equal.

In one embodiment, a collimator allows for multi-axis adjustment either manually by hand or automatically with actuators.

In one embodiment, software monitoring of source alignment energy levels provide instant feedback and alarm/notify when drift is outside safe operating parameters and alignment is needed.

In one embodiment, an automated process of performing photodiode array energy balancing plate corrections is provided by controlling the belt and the imaging system to perform the correction by stepping through power levels without operator intervention.

In one embodiment, a collimator is provided that is not fixed but that has multiple axis's of adjustment for the alignment.

In one embodiment, a graduated step plate fixture is incrementally passed step by step, one step at a time, under the X-ray beam to allow automated capture of each plate thickness. Once the optimum alignment and plate correction values are found, they are stored for later comparison to the real-time values generated while the scanner is performing inspections. Based on the comparisons, if a parameter is detected outside predetermined values, the scanner and alarm and corrective action may be taken. The collimator design allows for placement of devices which can automatically adjust the alignment to a known light gathering point for each PDA.

Existing collimators are fixed and can only be adjusted by removing a fan shield to access them. This is a time consuming process. The present disclosure will allow the vision inspection system, such as an X-ray scanner, the ability to stay optimized producing high quality images for a much longer period and in many different environments. The disclosure provides improvements in vision systems that will speed the imaging system set-up and allow for remote and automated optimization of the image acquisition system. The ability to automatically plate correct will reduce unwanted errors and decrease the overall cost of the system providing a pricing and performance advantage.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Conventional X-ray scanners use a static collimator to modify the X-ray beam into a high aspect rectangular shape (fan beam) to project onto a moving conveyor belt. The fan beam of X-rays generally coincides with the width of the conveyor belt on which items to be scanned are placed. The static collimator is adjusted at the time of manufacture of the scanner. If the collimator goes out of spatial adjustment, possibly resulting in an uneven fan beam or even part of the fan beam not been sensed by the detector, a technician would need to be dispatched to the scanner's location globally as needed to re-adjust manually.

Furthermore, other parameters of the X-ray source need to be adjusted as well to produce an optimum fan beam. To perform a plate correction to determine the proper X-ray source parameters manually is a time consuming process. Each plate would need to be sent through the X-ray scanner with an image captured at each plate thickness. This could be anywhere from 8-16 different images. Once the images are taken and their values manually gathered they would need to be placed into an equation to find the optimal value for each photodiode array (PDA) so that they can be corrected for the variation in the light and energy transmission they detect. Periodic testing is performed by an operator to verify operation. Normally daily, but is a time consuming manual process.

In one embodiment of this disclosure, a scanner 100 uses an electromagnetic wave source 102 and a detector 110 to analyze items for defects or impurities. Although the present disclosure uses an X-ray source and detector as a representative embodiment, the disclosure is not thereby limited, since the disclosure can apply to any electromagnetic wave source and detector.

X-ray equipment can be difficult to keep adjusted for optimal image quality. When the source 102 and detector 110 go out of alignment image quality and overall performance suffers. The cost to maintain the level of performance can be very high.

In this disclosure, a spatially adjustable collimator 108 and automated methods to keep the image system optimized and the detector properly plate corrected are provided to ensure higher periods of optimal performance and much lower cost of ownership.

Figure 1:
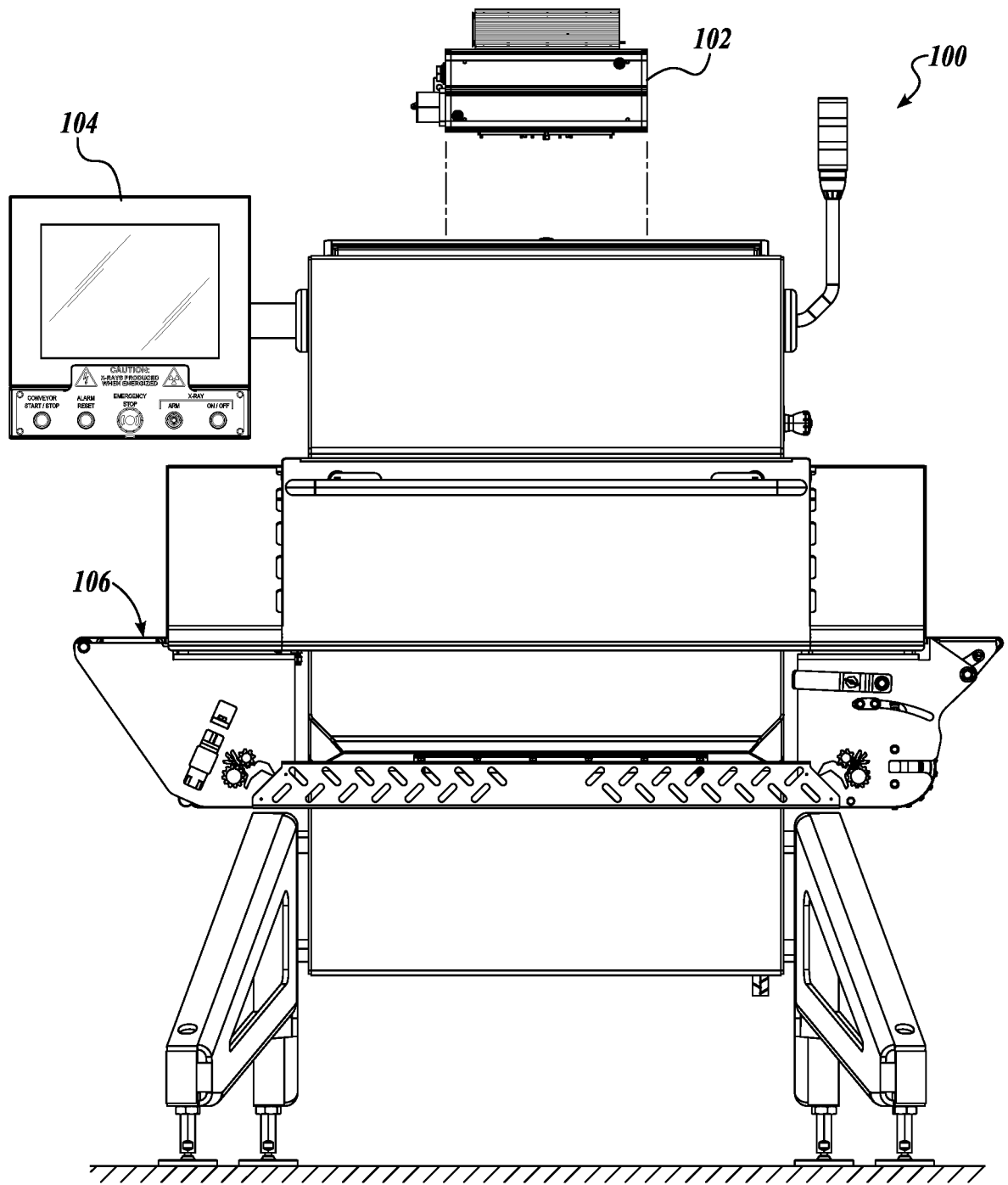
FIG. 1 is an illustration of a scanner in accordance with one embodiment.

FIG. 1 is an illustration of one embodiment of a scanner 100 that comprises an X-ray source 102. The scanner 100 can be integrated into any manufacturing line that requires that inspection of items.

In one exemplary embodiment, the scanner 100 may be used to detect for the presence of foreign bodies in food, such as, metal, rocks, bone, and the like.

In one embodiment, the scanner 100 may be used to detect defects of foods and other products, such as undersized or oversized portions, excessive fat content, off-colors, irregularity in shape, and the like.

In one embodiment, the scanner 100 comprises the X-ray source 102 that emits X-rays that pass through a collimator 108 (shown in FIG. 2), and then are directed to the conveyor belt 106 surface carrying the items 112 to be scanned.

In one embodiment, the scanner 100 further includes a human machine interface (HMI) 104 and the conveyor belt 106 for continually moving the items 112 to be scanned under the X-ray source 102 and collimator 108.

Figure 2:
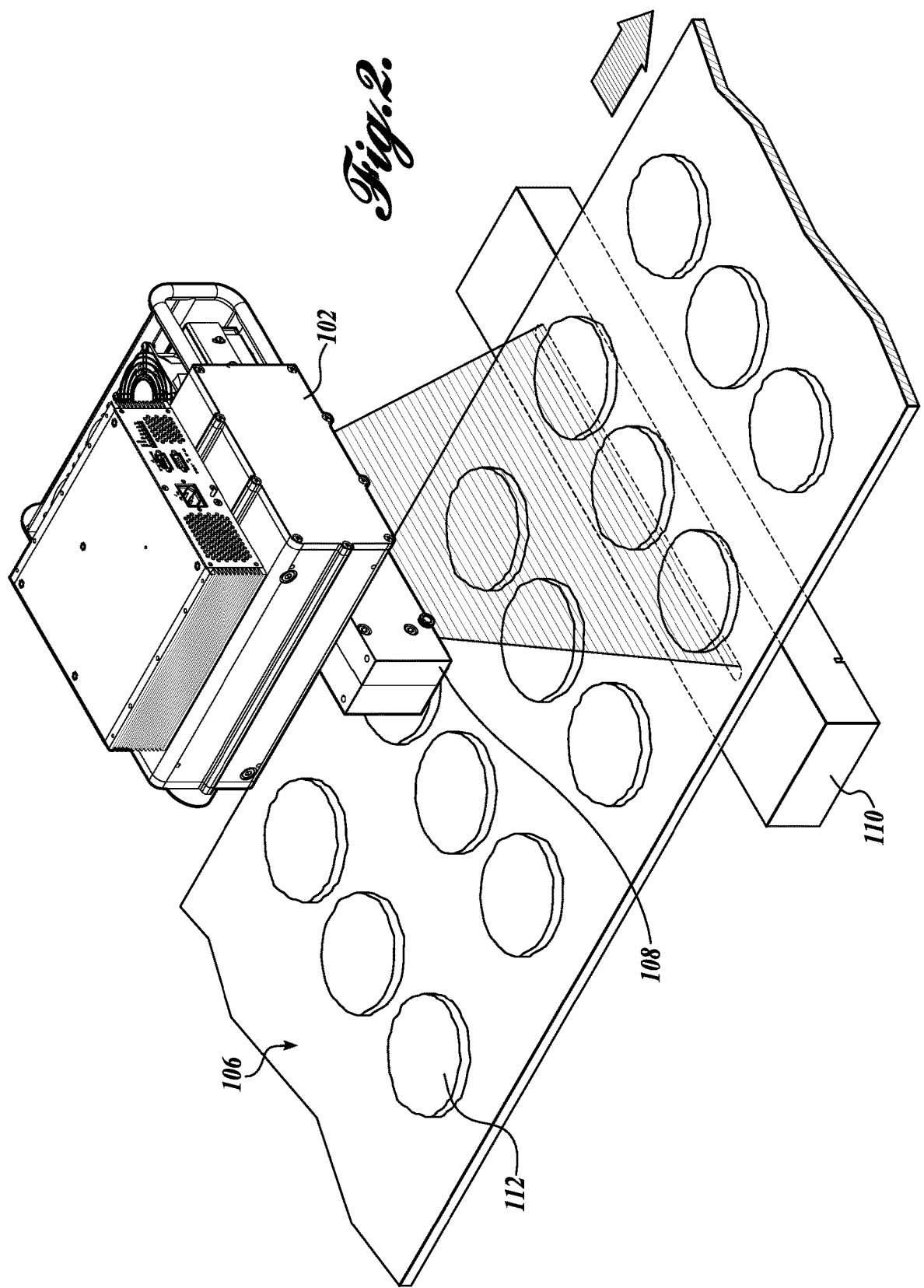
FIG. 2 is a detailed illustration of the electromagnetic wave source, the electromagnetic energy detector, and a conveyor belt of the scanner of FIG. 1.

Referring to FIG. 2, the X-ray source 102, collimator 108, conveyor belt 106, and detector 110 are being illustrated in isolation from the scanner 100. The collimator 108 is positioned between the X-ray source 102 and the upper surface of the conveyor belt 106.

The collimator 108 is used to alter the shape of the X-ray beam to be useful in scanning across the conveyor belt 106. The X-ray source 102 provides a conical beam of X-ray emissions that emanate from one point in the X-ray tube that is contained in the X-ray source 102. To reduce the amount of emissions the X-ray beam is collimated to a fan shaped beam 154 by the collimator 108. This creates a high aspect rectangular footprint on the detector 110.

The footprint can ideally be the same size as the imaging pickup area on the detector 110. The detector 110 is positioned below the conveyor belt 106 and senses the X-rays that pass through the items 112 and conveyor belt 106. The detector 110 can sense for example, the flux, spatial distribution, spectrum, and other properties of X-rays.

Various technologies can be used in the detector 110. In one embodiment, the detector 110 comprises photodiode arrays (PDAs). The detector 110 includes a linear series of PDAs which creates a collector for a line scan. The scanner 100 is optimized in performance and works properly when the X-ray source fan beam is aligned with the detecting elements from the detector 110. By spatially adjusting the collimator 108, the shape of the X-ray fan beam can be adjusted as well as the alignment of the fan beam footprint on the detector 110.

Figure 3:
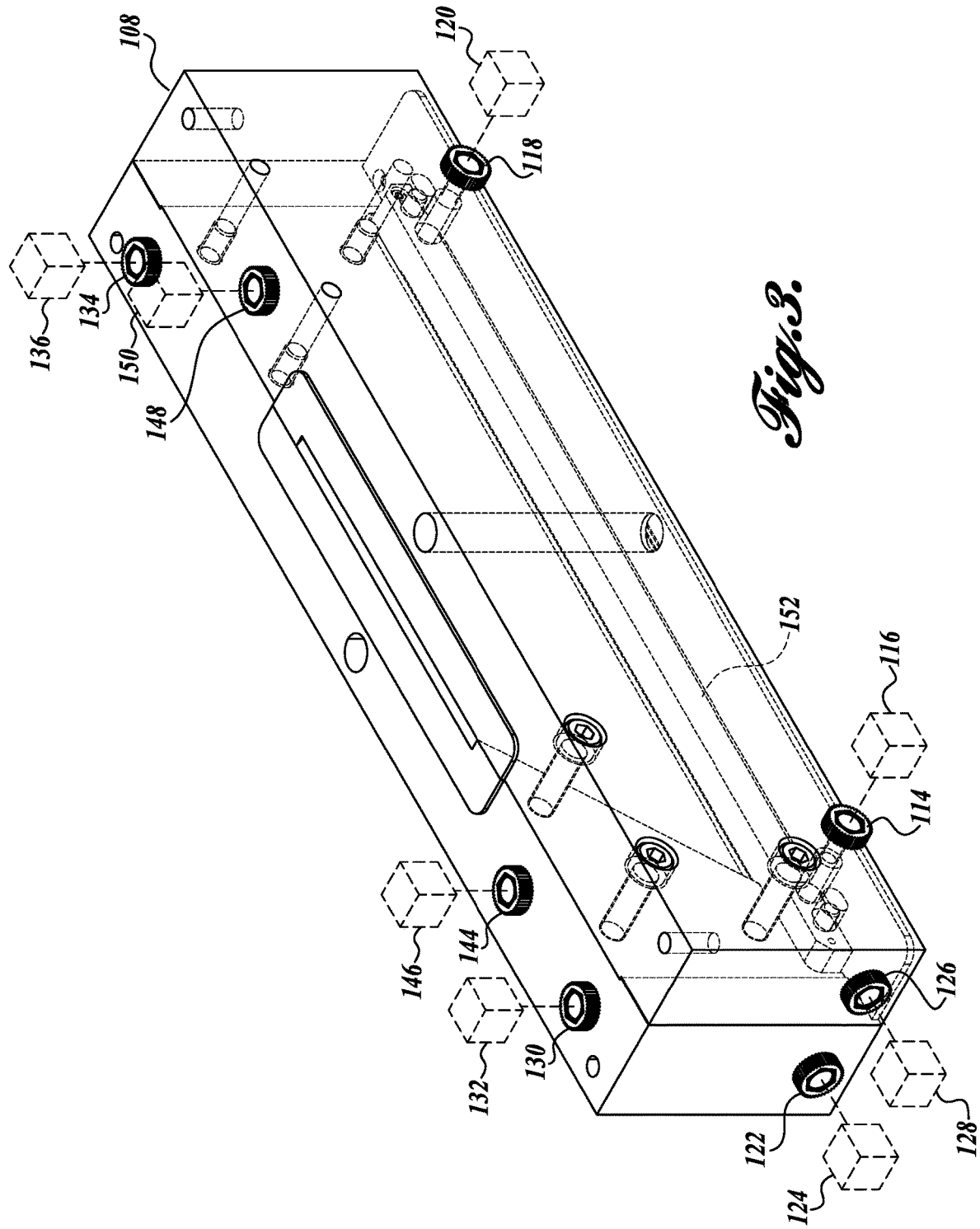
FIG. 3 is an illustration of a spatially-adjustable collimator of the electromagnetic wave source.

Referring to FIG. 3, the collimator 108 provides a fan shaped X-ray beam 154 through the use of one or more shielding elements 152.

The internal shielding elements 152 (lead, brass, tungsten and others) are inside a fixed housing block and are adjustable from the outside of the housing block with adjusting mechanisms.

In accordance with this disclosure, the collimator 108 is adjustable to alter the electromagnetic beam 154 by including the ability to make adjustments to the internal shielding elements 152 both in translation in a straight line and angular rotation in 3-axes to adjust the fan beam footprint striking the detector 110.

In one embodiment, the collimator 108 is comprised of adjustable elements allowing a technician to make the alignment of the fan beam 154 either manually without tools or automatically with optional actuators.

In one embodiment, fine adjusting screws are used to translate and/or rotate the internal shielding elements 152 of the collimator 108, and thus, change the energy levels of the electromagnetic beam striking the detector 110.

Fine adjusting screws allow the amount of travel to be calculated by using the pitch or TPI (threads per inch) to determine how many linear micrometers per revolution the screw moves. In one embodiment, the adjusting screws are turned by automatic actuators.

In one embodiment, fine adjusting screws are replaced by linear automatic actuators that include a linear displacement rod that causes the movement in the internal shielding elements 152 of the collimator 108.

In one embodiment, pairs of adjusting mechanisms are placed on opposite sides of a center pivot for each axis of the collimator 108. For example, referring to FIGS. 3 and 4a, 4b, and 4c, x-axis oriented linear adjusting mechanisms 114 and 118 positioned on respective ends of the collimator 108 y-dimension can translate the internal shielding elements 152 of collimator 108 side to side along the x-axis without changing the angle (i.e., without rotation) as illustrated in FIG. 4a by moving each adjusting mechanisms 114 and 118 the same amount in the same direction.

The same two adjusting mechanisms 114 and 118 can be used to rotate the internal elements 152 of the collimator 108 clockwise or counterclockwise with respect to the vertical z-axis at 138 by moving the adjusting mechanisms 114 and 118 in opposite directions or by moving one adjustment mechanism more than the other.

Figure 4A:
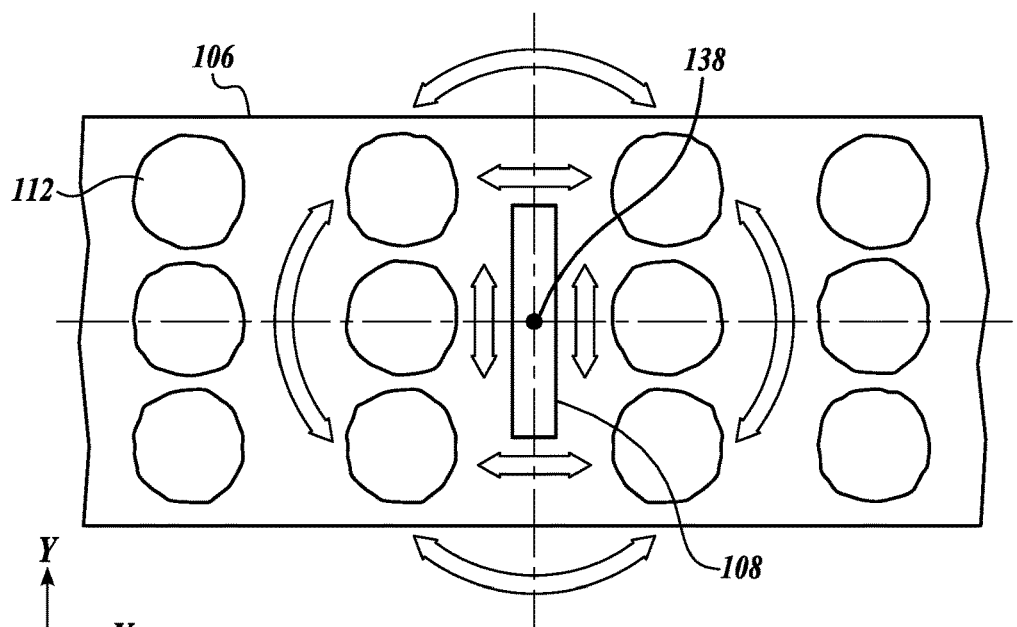
FIG. 4a is a schematic illustration showing the range of spatial adjustment of the collimator in a 3-axis coordinate system.

Y-axis oriented linear adjusting mechanisms 122 and 126 positioned on respective sides of the collimator 108 x-dimension can translate the internal shielding elements 152 of the collimator 108 front and back along the y-axis without changing the angle (i.e., without rotation) as illustrated in FIG. 4a by moving each adjusting mechanisms 122 and 126 the same amount in the same direction.

The same two adjusting mechanisms 122 and 126 can be used to rotate the internal shielding elements 152 of the collimator 108 clockwise or counterclockwise with respect to the vertical z-axis at 138 by moving the adjusting mechanisms 122 and 126 in opposite directions or by moving one adjustment mechanism more than the other.

Figure 4B:
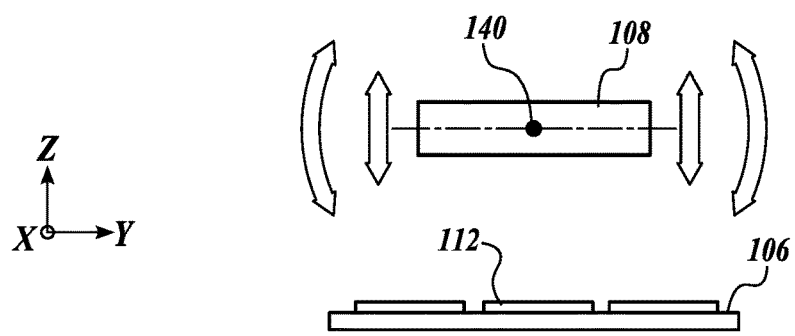
FIG. 4b is a schematic illustration showing the range of spatial adjustment of the collimator in a 3-axis coordinate system.

Referring to FIGS. 3 and 4b, z-axis oriented linear adjusting mechanisms 130 and 134 positioned on respective ends of the collimator 108 y-dimension can translate the internal shielding elements 152 of the collimator 108 up and down along the z-axis without changing the angle (i.e., without rotation) as illustrated in FIG. 4b by moving each adjusting mechanisms 130 and 134 the same amount in the same direction.

The same two adjusting mechanisms 130 and 134 can be used to rotate the internal shielding elements 152 of the collimator 108 clockwise or counterclockwise with respect to the horizontal x-axis at 140 by moving the adjusting mechanisms 130 and 134 in opposite directions or by moving one adjustment mechanism more than the other.

Figure 4C:
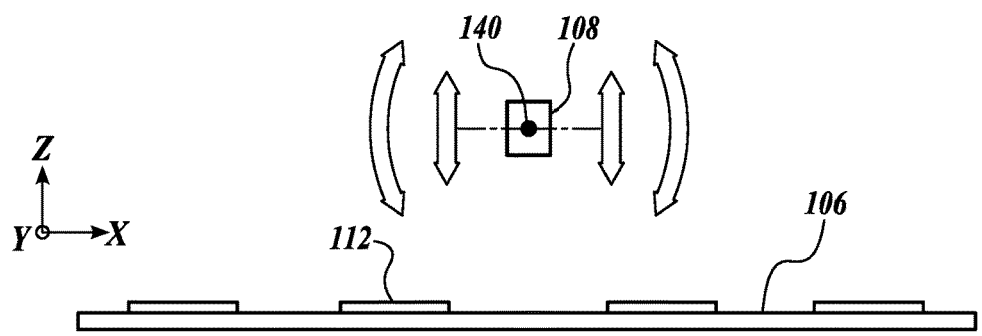
FIG. 4c is a schematic illustration showing the range of spatial adjustment of the collimator in a 3-axis coordinate system.

Referring to FIGS. 3 and 4c, z-axis oriented linear adjusting mechanisms 144 and 148 positioned on respective sides of the collimator 108 x-dimension can translate the internal shielding elements 152 of the collimator 108 up and down along the z-axis without changing the angle (i.e., without rotation) as illustrated in FIG. 4c by moving each adjusting mechanisms 144 and 148 the same amount in the same direction.

The same two adjusting mechanisms 144 and 148 can be used to rotate the internal shielding elements 152 of the collimator 108 clockwise or counterclockwise with respect to the horizontal y-axis at 142 by moving the adjusting mechanisms 144 and 148 in opposite directions or by moving one adjustment mechanism more than the other.

The adjusting mechanisms can also have locking elements to lock the internal shielding elements 152 of the collimator 108 into position.

In the event of automatic actuators, the control system components would provide the measurements and automatically lock the internal shielding elements 152 of the collimator 108 into the optimum position.

Therefore, the internal shielding elements 152 of the collimator 108 can translate in 3-axes, and also pitch, roll, and yaw in the 3-axes.

In other embodiments, the pitch, roll, and yam movement can be achieved by the use of a ball pivot on a translatable plate, or a combination of any adjusting mechanisms can be used.

In one embodiment, springs can be used in place of one of the pair of the adjusting mechanisms to counteract the movement of a single adjusting mechanism.

Any movement of the internal shielding elements 152 of the collimator 108 in either translation or rotation about any one or more of the axes will cause a change in the parameters received by the detector 110.

To observe the results of the adjustments to obtain feedback, the HMI 104 can be positioned to the back of the scanner 100 where the adjustments are performed and can be observed on a display screen.

Figure 5:
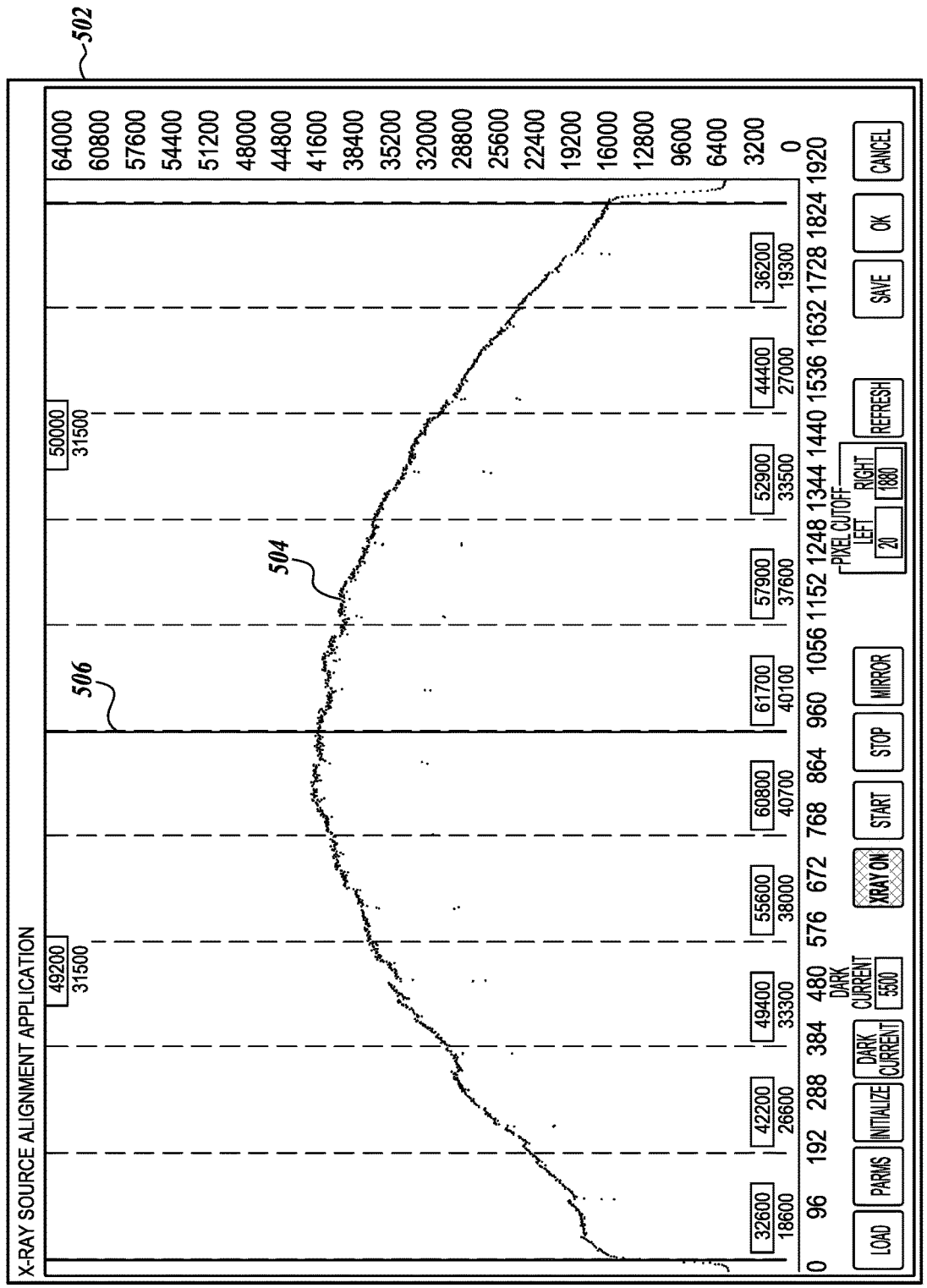
FIG. 5 is an illustration of a display of a human machine interface showing a representative electromagnetic energy level curve an electromagnetic beam.

FIG. 5 is an illustration of a representative display 502 of the HMI 104 that can be used to adjust the spatial alignment of the internal shielding elements 152 of the collimator 108.

In one embodiment, the HMI 104 can provide real-time feedback in the form of a graph depicting the energy levels detected by the detector 110 as well as provide numerical values of the energy levels at the present time, which can be used in the manual spatial adjustment of the internal shielding elements 152 of the collimator 108.

FIG. 5 shows a curve 504 representing the energy level at the footprint of the fan beam detected by the detector 110 along the y-axis, which also represents the energy level across the width of the conveyor belt 106.

Ideally, the right and left sides of the curve 504 should be symmetrical with respect to the midpoint 506. The horizontal axis represents the pixel count. Vertical dashed lines show the division between stacked photodiode arrays, so that the readings between any two vertical dashed lines represent one photodiode array. In one embodiment, multiple photodiode arrays are stacked together in the detector 110 to cover the width of conveyor belt 106.

The lower number between any two vertical lines is the currently measured energy level reading, while the number in the box is the target energy level, predetermined from a previously recorded correct alignment.

The units on the vertical scale are normalized units representing the energy levels. The units on the vertical scale represent a 16 bit value (0 to 65535) corresponding to intensity.

Accordingly, the graph of FIG. 5 is a useful tool for the operator when manually aligning the internal shielding elements 152 of the collimator 108.

In a manual adjustment, the operator attempts to have both the left and right sides of the curve 504 be the same shape, while also attempting to maximize the energy levels to the target values, for example.

In the automated spatial adjustment done by the control system components, the operator can view the results of automatic spatial adjustment on the display, however, the control system components comprising of the CPUs 600 and storage medium 602 are performing the optimization of the energy levels to have matching and maximized energy levels on the left and right sides of the curve 504.

In one embodiment, the spatial adjustments of the internal shielding elements 152 of the collimator 108 can be automated and controlled by one or more central processing units communicating with actuators via wired or wireless signal carrying means.

Referring to FIG. 3, an actuator is provided for each one of the adjusting mechanisms. Actuators can be one of several types, such as, rotating actuators, linear actuators, servo DC motors, pneumatic actuators, or hydraulic actuators, for example. The actuators receive a signal that determines a predetermined amount of movement from the actuator.

Actuator 116 is connected to and moves the adjusting mechanism 114. Actuator 120 is connected to and moves the adjusting mechanism 118. Actuator 124 is connected to and moves the adjusting mechanism 122. Actuator 128 is connected to and moves the adjusting mechanism 126. Actuator 132 is connected to and moves the adjusting mechanism 130. Actuator 146 is connected to and moves the adjusting mechanism 144. Actuator 150 is connected to and moves the adjusting mechanism 148. Actuator 136 is connected to and moves the mechanism 134.

Figure 6:
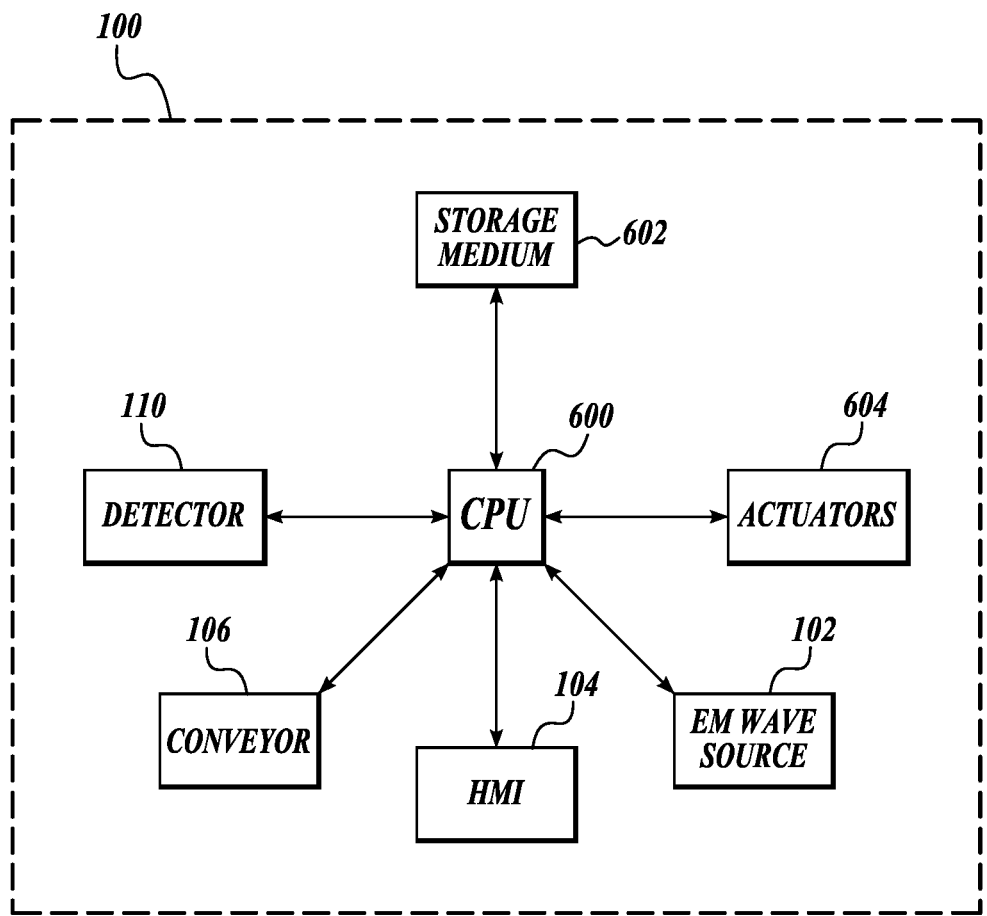
FIG. 6 is a schematic illustration of several components comprising the control system of the scanner of FIG. 1.

FIG. 6 is a schematic illustration of some of the components that make up a control system. The control system comprises various components that communicate with one another to carry out certain routines or methods to operate the scanner 100.

In one embodiment, the scanner 100 includes one or more central processing units 600. The central processing units 600 include the electronic circuitry that carries out instructions of software or firmware by performing the basic arithmetic, logic, controlling, operating system, and input/output operations specified by the instructions.

Although FIG. 6 shows an embodiment where the scanner 100 includes the one or more CPUs 600, in another embodiment, the CPUs 600 can reside externally from the scanner 100, for example in a remote server providing Cloud computing resources.

In one embodiment, the scanner 100 is located at a customer's physical location, and the CPUs 600 reside in a remote server at the service vendor (e.g. the provider or manufacturer of the scanner, or a Cloud computing service provider).

In one embodiment, the scanner 100 includes a tangible non-transitory storage medium/computer readable medium 602 that communicates with the one or more processing units 600.

Although FIG. 6 shows an embodiment where the scanner 100 includes the storage medium 602, in another embodiment, the storage medium 602 can reside externally from the scanner 100, for example in a remote server providing Cloud computing resources.

In one embodiment, the scanner 100 is located at a customer's physical location, and the storage medium 602 resides in a remote server at the service vendor (e.g. the provider or manufacturer of the scanner, or a Cloud computing service provider).

The storage medium 602 in addition to storing an operating system can store firmware or software to perform a set of instructions for performing methods for calibrating including aligning the internal shielding elements 152 of the collimator 108 and a stepping algorithm as described further below.

Furthermore, the storage medium 602 can be used to store predetermined models of an optimized X-ray fan beam, energy levels, and footprint that is used for comparing to the actual X-ray fan beam footprint and energy levels being generated at any moment.

The storage medium can also be used for storing the amount of movement in the actuators in relation to a control signal.

The one or more CPUs 600 communicate with each of the actuators, collectively referred to by the reference 604 in FIG. 6.

Control signals sent to the automatic actuators can be in the range of a certain voltage.

The one or more CPUs 600 also communicate with the detector 110.

Detector 110 sends signals to the one or more CPUs 600 that the CPUs 600 interpret into an X-ray fan beam footprint, energy levels, and other parameters that the one or more CPUs 600 can compared to the parameters of an optimized X-ray fan beam footprint.

For example, the CPUs 600 can carry out statistical algorithms to analyze data. Such statistical algorithms can use principal component analysis, ANOVA, clustering methods, and linear regression, for example.

The one or more CPUs 600 also communicate with the electromagnetic wave source 102 (e.g., X-ray source).

The one or more CPUs 600 can control the on or off state of the electromagnetic wave source 102.

The one or more CPUs 600 can control the energy level, wavelength, and the like of the electromagnetic wave source 102.

The one or more CPUs 600 can control the conveyor belt 106. The one or more CPUs 600 can control the on or off state of the conveyor 106 to synchronize with the detector 110.

The one or more CPUs 600 can control the linear speed of the conveyor 106 to synchronize the speed with the detector 110.

The one or more CPUs 600 also communicate with the HMI 104. The HMI 104 can include a touch display to allow the operator to start and set operating functions of the scanner 100. For example, the HMI 104 can have menus for the operator to select various parameters for running the scanner.

In one embodiment, the scanner 100 includes a menu and/or a display for the operator to start and run an automatic alignment method. In one embodiment, the scanner 100 includes a menu and/or a display for the use to start and run an automatic plate correction method.

Figure 7:
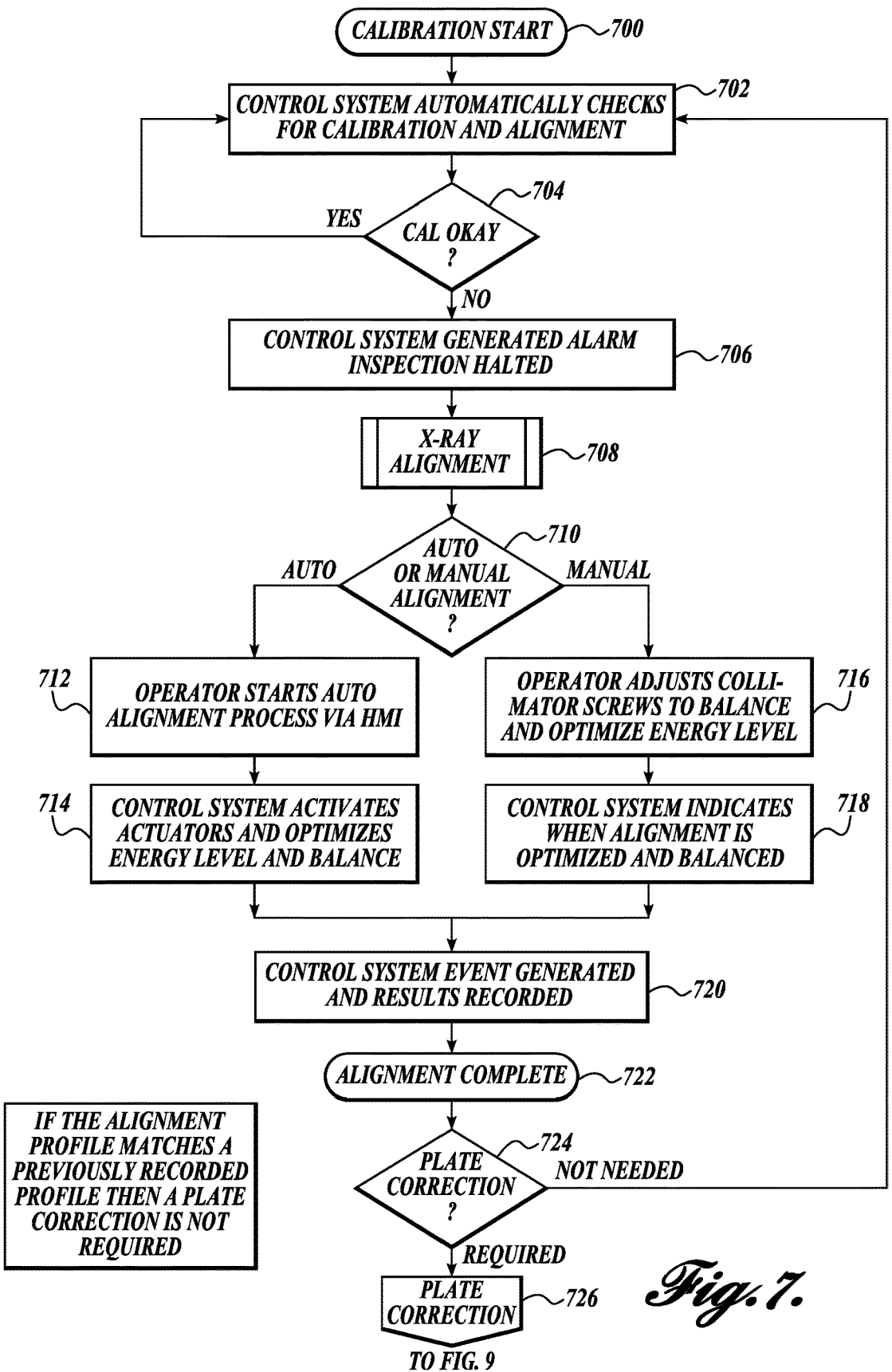
FIG. 7 is a flow diagram of an alignment method of the collimator.

Referring to FIG. 7, a method implemented by the scanner 100 is illustrated.

In one embodiment, the scanner 100 has the ability to automatically monitor the shape and energy level symmetry across the entire detector 110, for example.

A representative shape of the detected energy levels across the detector 110 is illustrated in FIG. 5. If any of the energy levels that comprise the curve 504 (FIG. 5) is not within predetermined limits, the scanner 100 can generate an alarm. Then, the scanner 100 can be manually or automatically aligned.

As used herein, alignment can be a part of calibration. Calibration is a term including alignment, plate correction and profiles for product.

Figure 9:
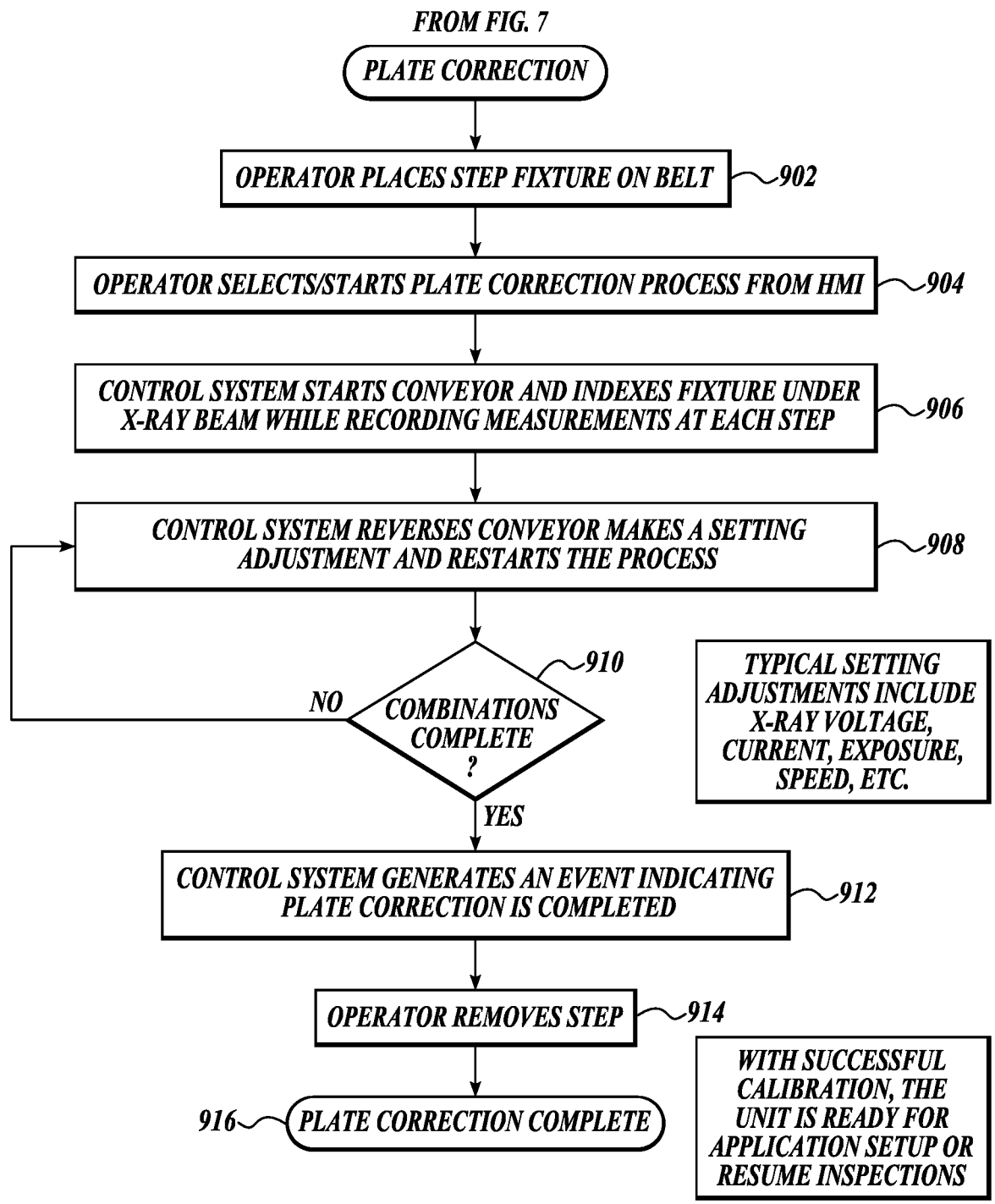
FIG. 9 is a flow diagram of a plate correction method of the electromagnetic energy detector.

The set of instructions for performing methods in accordance with FIGS. 7 and 9 may be implemented, in some cases, in hardware, firmware, software, or any combination thereof. Methods of FIGS. 7 and 9 can be computer-implemented methods.

The disclosed embodiments may also be implemented as instructions carried by or stored on one or more transitory or non-transitory tangible machine-readable (e.g., computer-readable) storage medium 602, which may be read and executed by the one or more processors 600.

A machine-readable storage medium 602 may be embodied as any storage device, mechanism, or other physical structure for storing or transmitting information in a form readable by a machine (e.g., a volatile or non-volatile memory, a media disc, or other media device).

In block 702, the control system components continually and automatically check for calibration including alignment during the routine or normal inspection of the items 112 being scanned to determine whether any parameters of the energy level curve 504 is outside of predetermined limits.

In one embodiment, the control system components include the one or more processors 600.

In one embodiment, the control system components include at least the one or more processors 600 and the storage medium 602.

In one embodiment, the control system components include at least the one or more processors 600, the storage medium 602, and the HMI 104.

The one or more processors 600 communicates by sending and receiving signals to and from the detector 110, the conveyor belt 106, the HMI 104, the electromagnetic wave source 102, and the actuators 604.

In one embodiment, alignment is checked by comparing the present measured curve 504 and energy levels to an optimal shape and energy levels that are stored in the storage medium 602. Storage medium 602 can have a plurality of predetermined optimal energy level curves, based on the particular application of the scanner.

Prior to running an inspection application, the operator can use the HMI 104 to initially set the scan parameters, the material being scanned, and the purpose of the scan among other settings.

Optimal energy level curves can depend on the item being scanned. For example, a different optimal energy level curve can be used for chicken breasts as compared to hamburgers, and also depending on the purpose of the application, such as scanning for metal versus scanning for the amount of fatty material.

From block 702, the method enters block 704. In block 704, for each of the calibration and alignment parameters tested in block 702, the control system components determine whether such parameter is within predetermined limits.

If the answer to the test in block 704 is yes, the method returns to block 702 to continue the inspection of items being scanned and to continue testing the remaining parameters.

If the answer to the test in block 704 is no, the method goes to block 706 to generate an alarm and a signal is sent by the control system components to halt inspection. For example, the conveyor belt 106 can be stopped. This monitoring enables the control system components to notify the operator immediately and/or shutdown the scanner 100 in the event of any issues including drift, misalignment, detector and/or source failures among other problems.

From block 706, the method enters block 708. Block 708 is a subroutine to align the elements 152 of the collimator 108. In block 710, the method checks whether the alignment of the collimator 108 is to be performed manually or automatically.

The operator can select manual or automatic alignment via the HMI 104 depending on whether the collimator is provided with automated actuators. If the operator selects Manual alignment, the method enters block 716.

In block 716, the operator adjusts the collimator adjusting mechanisms to balance and optimize the energy level as discuss above in relation to FIG. 5. After each incremental change to one or more of the adjusting mechanisms, the operator can check the effect of the change on the HMI 104 display (see FIG. 5). From block 716, the method enters block 718.

In block 718, after every change made by the operator, the control system components indicate when the alignment is optimized and balanced by comparing the current shape 504 and energy levels to the optimized and balanced shape stored in the computer medium 602.

If the operator selects Automatic in block 710, because the automatic actuators 604 are provided with each adjusting mechanism, the method enters block 712.

In block 712, the operator starts the automatic alignment process from the HMI 104. From block 712, the method enters block 714.

In block 714, the control system components activate the actuators 604 to optimize energy levels and balance the shape 504. For example, in one embodiment, each of the actuators connected to each of the adjusting mechanisms is stepped one predetermined increment at a time. In other embodiments, more than one of the actuators is incremented.

The scanner 100 may have a machine learning algorithm where patterns are recognized from past misalignment events to assist in recognizing misalignment patterns in the present and future misalignment events. Then, once a misalignment is recognized as having occurred in the past, the actuators can initially be set to the settings matching those of a previously corrected misalignment event, and then begin incremental adjustment from the initial alignment settings, if needed. The machine learning algorithm can save significant time to reach the optimal alignment, shape, and energy levels.

As with the Manual feature, the Automatic feature relies on the control system components to indicate when the alignment is optimized and balanced by comparing the current shape 504 and energy levels to the optimized and balanced shape stored in the computer medium 602. From block 718 or block 714, the method enters block 720.

In block 720, the control system event is generated and recorded, including the shape and the energy levels across the beam footprint and that matching output of each of the actuators 604, and the method enters block 722 indicating that the alignment is complete.

From block 722, the method enters block 724. In block 724, the method determines whether plate corrections are required. In one embodiment, whether or not plate correction is required is determined by assessing whether the alignment profile matches a previously recorded profile.

In one embodiment, an alignment profile includes, but is not limited to, the source voltage, source current, and detector integration time. In addition, an alignment curve is saved for each combination of these parameters.

Due to the geometry of the X-ray source 102 which needs to spread the X-ray beam across the width of the conveyor belt 106, the closest point of the detector 110 to the X-ray source sees the highest energy level, and the detector 110 should read energy levels that diminish generally proportionately and continuously extending away from the closest point.

The plate correction method described in relation to FIG. 9 is used to balance the energy levels detected by the photodiode arrays in the detector 110. Therefore, various parameters of the X-ray source are manipulated to enable testing to determine the combination that produces a generally continuous, generally proportionate curve 504. Then, each photodiode array can be corrected for the variation in the light and energy transmission they detect. It should be noted that this disclosure is not limited to PDA type detectors, other detectors may use CCD, CMOS and others.

Plate corrections generate mapping tables that maximize the image information in subsequent processing. The plate corrections can be complicated and time consuming and are needed for every alignment profile.

According to this disclosure, the process of plate correction is automated and performed by the control system components including the one or more central processing units 600 and the storage medium 602.

Figure 8:
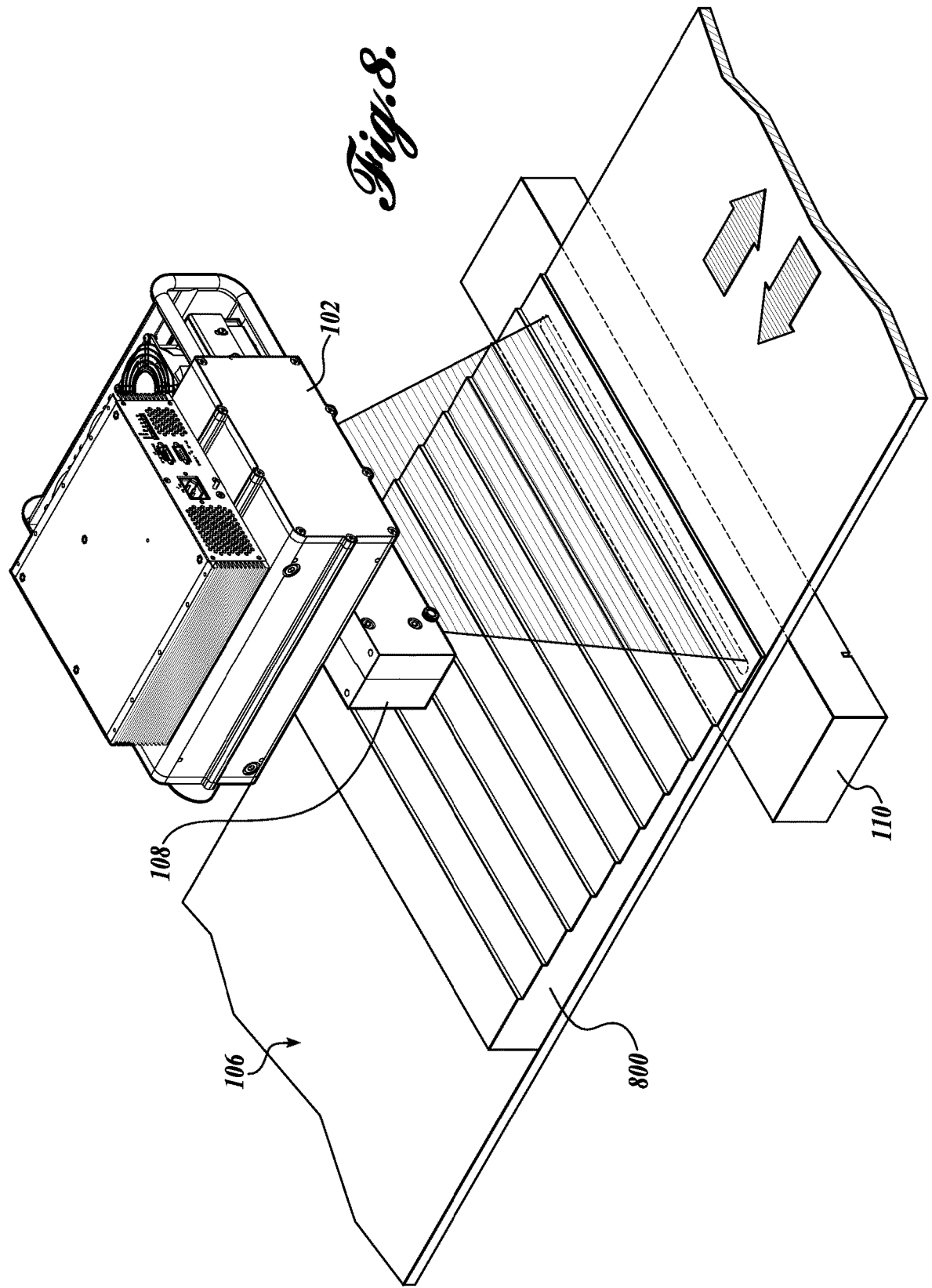
FIG. 8 is an illustration of an apparatus to perform plate corrections.

The process is started by inserting a step plate fixture 800 as illustrated in FIG. 8. The step plate fixture 800 is made from a material generally transparent to X-rays, but that will absorb some of the X-rays so that the thicker parts of the step plate fixture 800 will cause lower energy to be detected at the detector 110. Suitable materials include, but are not limited to, aluminum, plastics, and tissue equivalent phantoms.

In one embodiment, the step plate fixture 800 is at least as wide as the fan beam or wider.

In one embodiment, the step plate fixture 800 includes discrete steps of increasing thickness (height) from one end to the opposite end. In one embodiment, the difference in height (rise) between one step and the next step is constant.

In one embodiment, the step plate fixture 800 has a minimum thickness at one end corresponding to a single step. The step plate fixture 800 has a maximum thickness at the opposite end corresponding to the maximum number of steps. In one embodiment, the length (run) of each step is constant.

In one embodiment, the step plate fixture 800 is a monolithic piece of material.

In one embodiment, the step plate fixture 800 comprises a plurality of discrete pieces.

The control system components will control the belt 106 in such a way as to index the step plate fixture 800 under the X-ray beam and record the results. X-ray source 102 power levels will be increased automatically and the fixture 800 will automatically be repositioned and reprocessed, and the results are recorded at all required levels. These results will be stored and used in the automatic monitoring of the scanner 100.

Referring to FIG. 9, a flow diagram is used to illustrate the plate correction method.

In block 902, the operator places the step plate fixture 800 on the conveyor belt 106 such that the steps increase along the length of the conveyor belt 106. The step plate fixture 800 can be square with the electromagnetic fan beam 154, so that all of the electromagnetic fan beam 154 can hit the same step. From block 902, the method enters block 904.

In block 904, the operator selects from a menu the plate correction feature from the HMI 104. From block 904, the method enters block 906.

In block 906, the control system components start the conveyor belt 106 and the X-ray source 102, and then indexes the step plate fixture 800 under the fan beam while recording measurements at each step with the same parameter settings.

Manipulated parameters that may be tested one at a time include X-ray voltage, current, exposure time, speed, and the like. From block 906, the method enters block 908.

In block 908, the control system components reverse the direction of the conveyor belt 106 or bring the conveyor belt 106 to the first lowest step.

In block 908, the control system components can also make a setting adjustment to at least one of the test parameters and restart recording the measurements at each step with the updated parameter settings, such that after each change in the set of parameters, the step plate fixture 800 is incrementally moved step by step to expose each of the plurality of steps to the electromagnetic beam at each subsequent set of changed parameters. From block 908, the method enters block 910.

In block 910, the control system components continually check whether the predetermined range of parameter setting combinations is complete. If the control system components determine that all the combinations have been tested, the method enters block 912.

In block 912, the control system components generate an event indicating plate correction is completed and issues a notice on the HMI 104, and the data is stored in the storage medium 602. From block 912, the method steps to block 914, where the operator can remove the step plate fixture 800 from the conveyor belt 106, and the plate correction is completed in block 916. After completion of the plate correction method, the scanner 100 is ready to setup a new inspection protocol or to continue the current inspection protocol.

In another embodiment of the plate correction method, the combinations of manipulated parameters can be tested at each step, and then, the step plate fixture can be incrementally moved to the next step, wherein again, all combinations of the manipulated parameters are tested for the second and subsequent steps.

In one embodiment, a scanner 100 comprises an electromagnetic wave source 102; a collimator 108 positioned to alter the electromagnetic waves emitted from the electromagnetic wave source into an electromagnetic beam 154; and a detector 110 positioned to measure one or more levels of electromagnetic energy of the electromagnetic beam, wherein a collimator element 152 is spatially adjustable in at least one axis via one or more adjusting mechanisms 114, 118, 122, 126, 130, 134, 144, 148 to change the one or more levels of the electromagnetic energy measured the detector.

In one embodiment, the electromagnetic wave source 102 generates X-rays.

In one embodiment, a footprint of the electromagnetic beam 154 comprises a high aspect rectangular shape.

In one embodiment, a collimator shielding element 152 is spatially adjustable to translate and rotate in at least one axis.

In one embodiment, a collimator shielding element 152 is spatially adjustable to translate and rotate in three axes.

In one embodiment, the detector 110 comprises a stack of photodiode arrays.

In one embodiment, the scanner 100 comprises a conveyor belt 106 juxtaposed between the collimator 108 and the detector 110.

In one embodiment, the scanner 100 comprises one or more manually adjustable adjusting mechanisms 114, 118, 122, 126, 130, 134, 144, 148 to spatially adjust a collimator shielding element 152 without tools.

In one embodiment, the scanner 100 comprises one or more adjusting mechanisms 114, 118, 122, 126, 130, 134, 144, 148 coupled to actuators 116, 120, 124, 128, 132, 136, 146, 150 to spatially adjust a collimator shielding element with control system components.

In one embodiment, the control system components include at least a storage medium 602 and one or more central processing units 600 configured to communicate with the actuators.

In one embodiment, the scanner 100 comprises a human machine interface 104 configured to communicate with the one or more central processing units 600.

In one embodiment, the scanner 100 is configured to communicate with a storage medium 602 having instructions stored thereon to perform a method for detecting misalignment of the collimator 108, the method comprising:
  with the detector 110, measuring energy levels of the electromagnetic beam 154 produced by the collimator 108;
  with a control system 600, 602, comparing energy levels of the electromagnetic beam measured by the detector to predetermined values of energy levels of an aligned collimator; and
  spatially adjusting the collimator when a measured energy level measured by the detector is outside of a predetermined value.

In one embodiment, the scanner 100 is configured to communicate with a storage medium 602 having instructions stored thereon to perform a method for stepping through multiple combinations of parameters to gather data for balancing energy levels detected by a detector 100, the method comprising:
  with a control system 600, 602, operating the electromagnetic wave source 102 to generate an electromagnetic beam 154 at a plurality of combinations of parameters;
  with the control system, incrementally moving a step plate fixture 800 having a plurality of steps to expose the electromagnetic beam to a plurality of steps;
  with the control system, measuring one or more energy levels of the electromagnetic beam at more than one of steps and at more than one combination of parameters; and
  with the control system, selecting the combination of parameters that balances the energy levels detected by the detector.

In one embodiment, a tangible computer readable medium 602 is provided having instructions stored thereon to perform a method for detecting misalignment of a collimator 108, the method comprising, with a detector 110, measuring energy levels of an electromagnetic beam 154 produced by the collimator; with a control system 600, 602, comparing energy levels of the electromagnetic beam measured by the detector to predetermined values of energy levels of an aligned collimator; and spatially adjusting the collimator when a measured energy level measured by the detector is outside of a predetermined value.

In one embodiment, a tangible computer readable medium 602 is provided having instructions stored thereon to perform a method for stepping through multiple combinations of parameters to gather data for balancing energy levels detected by a detector 110, the method comprising, with a control system 600, 602, operating an electromagnetic wave source 102 to generate an electromagnetic beam 154 at a plurality of combinations of parameters; with the control system, incrementally moving a step plate fixture 800 having a plurality of steps to expose the electromagnetic beam to a plurality of steps; with the control system, measuring one or more energy levels of the electromagnetic beam at more than one of steps and at more than one combination of parameters; and with the control system, selecting the combination of parameters that most balances or maximizes the energy levels detected by the detector.

In one embodiment, a method is provided for detecting misalignment of a collimator 108, the method comprising, with a detector 110, measuring energy levels of an electromagnetic beam 154 produced by a collimator that alters electromagnetic waves produced by an electromagnetic wave source 102; with a control system 600, 602, comparing energy levels of the electromagnetic beam measured by a detector to predetermined values of energy levels of an aligned collimator; spatially adjusting the collimator when a measured energy level measured by the detector is outside of a predetermined value; and providing feedback of the present energy levels when a spatial adjustment is made to the collimator.

In one embodiment, the method comprises inspecting items 112 on a conveyor belt 106 passing through the electromagnetic beam 154.

In one embodiment, the method comprises halting inspecting the items 112 when a measured energy level is outside of a predetermined limit.

In one embodiment, the method comprises starting inspecting the items 112 after the collimator 108 has been spatially aligned.

In one embodiment, the method comprises spatially adjusting the collimator 108 with one or more actuators 116, 120, 124, 128, 132, 136, 146, 150 under the control of the control system 600, 602.

In one embodiment, the electromagnetic beam 154 comprises a high aspect rectangular footprint.

In one embodiment, a method is provided for stepping through multiple combinations of parameters to gather data for balancing energy levels detected by a detector 110, the method comprising, with a control system 600, 602, operating an electromagnetic wave source 102 to generate an electromagnetic beam 154 at a plurality of combinations of parameters; with the control system, incrementally moving a step plate fixture 800 having a plurality of steps to expose the electromagnetic beam to a plurality of steps; with the control system, measuring one or more energy levels of the electromagnetic beam at more than one of steps and at more than one combination of parameters; and with the control system, selecting the combination of parameters that most balances or maximizes the energy levels detected by the detector.

In one embodiment, the electromagnetic beam 154 comprises a high aspect rectangular footprint.

In one embodiment, the method comprises inspecting items 112 on a conveyor belt 106 passing through the electromagnetic beam.

In one embodiment, the most balanced energy levels comprises having the energy levels from both sides of the electromagnetic beam be most nearly equal.

While illustrative embodiments have been illustrated and described, it will be appreciated that various changes can be made therein without departing from the spirit and scope of the invention.

The invention claimed is:

1. A scanner, comprising:
    an electromagnetic wave source;
    a collimator positioned to alter the electromagnetic waves emitted from the electromagnetic wave source into an electromagnetic beam, wherein the collimator is configured to adjust a shape and alignment of the electromagnetic beam using one or more shielding elements, wherein a collimator shielding element is spatially adjustable to translate and rotate in three axes; and
    a detector positioned to measure one or more levels of electromagnetic intensity of the electromagnetic beam, wherein a collimator shielding element is spatially adjustable in at least one axis via one or more adjusting mechanisms to change the one or more levels of the electromagnetic intensity measured the detector.

2. The scanner of claim 1, wherein the electromagnetic wave source generates X-rays.

3. The scanner of claim 1, wherein a footprint of the electromagnetic beam comprises a high aspect rectangular shape.

4. The scanner of claim 1, wherein a collimator shielding element is spatially adjustable to translate and rotate in at least one axis.

5. The scanner of claim 1, wherein the detector comprises stacked photodiode arrays.

6. The scanner of claim 1, comprising a conveyor belt juxtaposed between the collimator and the detector.

7. The scanner of claim 1, comprising one or more adjusting mechanisms coupled to actuators to spatially adjust a collimator shielding element with control system components.

8. The scanner of claim 7, wherein the control system components includes at least a storage medium and one or more central processing units configured to communicate with the actuators.

9. The scanner of claim 7, comprising a human machine interface configured to communicate with the one or more central processing units.

10. The scanner of claim 1, wherein the scanner is configured to communicate with a storage medium having instructions stored thereon to perform a method for stepping through multiple combinations of parameters to gather data for balancing intensity levels detected by a detector, the method comprising:
    with a control system, operating the electromagnetic wave source to generate an electromagnetic beam at a plurality of combinations of parameters;
    with the control system, incrementally moving a step plate fixture having a plurality of steps to expose the electromagnetic beam to a plurality of steps;
    with the control system, measuring one or more intensity levels of the electromagnetic beam at more than one of steps and at more than one combination of parameters; and
    with the control system, selecting the combination of parameters that balances the intensity levels detected by the detector.

11. A scanner, comprising:
    an electromagnetic wave source;

a collimator positioned to alter the electromagnetic waves emitted from the electromagnetic wave source into an electromagnetic beam, wherein the collimator is configured to adjust a shape and alignment of the electromagnetic beam using one or more shielding elements; and a detector positioned to measure one or more levels of electromagnetic intensity of the electromagnetic beam, wherein a collimator shielding element is spatially adjustable in at least one axis via one or more adjusting mechanisms to change the one or more levels of the electromagnetic intensity measured the detector; and one or more manually adjustable adjusting mechanisms to spatially adjust a collimator shielding element without tools.

12. A scanner, comprising:

an electromagnetic wave source;

a collimator positioned to alter the electromagnetic waves emitted from the electromagnetic wave source into an electromagnetic beam, wherein the collimator is configured to adjust a shape and alignment of the electromagnetic beam using one or more shielding elements; and a detector positioned to measure one or more levels of electromagnetic intensity of the electromagnetic beam, wherein a collimator shielding element is spatially adjustable in at least one axis via one or more adjusting mechanisms to change the one or more levels of the electromagnetic intensity measured the detector, wherein the scanner is configured to communicate with a storage medium having instructions stored thereon to perform a method for detecting misalignment of the collimator, the method comprising:

with the detector, measuring intensity levels of the electromagnetic beam produced by the collimator;

with a control system, comparing intensity levels of the electromagnetic beam measured by the detector to predetermined values of intensity levels of an aligned collimator; and spatially adjusting the collimator when a measured intensity level measured by the detector is outside of a predetermined value.

13. A method for detecting misalignment of a collimator, the method comprising:

with a detector, measuring intensity levels of an electromagnetic beam produced by a collimator that alters electromagnetic waves produced by an electromagnetic wave source, wherein the collimator is configured to adjust a shape and alignment of the electromagnetic beam using one or more shielding elements;

with a control system, comparing intensity levels of the electromagnetic beam measured by a detector to predetermined values of intensity levels of an aligned collimator;

spatially adjusting the collimator when a measured intensity level measured by the detector is outside of a predetermined value; and providing feedback of the present intensity levels when a spatial adjustment is made to the collimator.

14. The method of claim 13, further comprising inspecting items on a conveyor belt passing through the electromagnetic beam.

15. The method of claim 14, further comprising halting inspecting the items when a measured intensity level is outside of a predetermined limit.

16. The method of claim 15, further comprising starting inspecting the items after the collimator has been spatially aligned.

17. The method of claim 13, further comprising spatially adjusting the collimator with one or more actuators under the control of the control system.

18. The method of claim 13, wherein the electromagnetic beam comprises a high aspect rectangular footprint.

* * * * *

UNITED STATES PATENT AND TRADEMARK OFFICE
CERTIFICATE OF CORRECTION

PATENT NO. : 12,044,634 B2
APPLICATION NO. : 17/635208
DATED : July 23, 2024
INVENTOR(S) : J. Gill et al.

It is certified that error appears in the above-identified patent and that said Letters Patent is hereby corrected as shown below:

On the Title Page

| Column | Line | |
|---|---|---|
| Page 2/ Item [57] | 9 | change "measured the" to -- measured by the --. |

In the Claims

| Column | Line | |
|---|---|---|
| 16 | 23 | Claim 1 change "measured the" to -- measured by the --. |
| 17 | 11 | Claim 11 change "measured the" to -- measured by the --. |
| 17 | 27 | Claim 12 change "measured the" to -- measured by the --. |

Signed and Sealed this
Sixth Day of May, 2025

Coke Morgan Stewart
*Acting Director of the United States Patent and Trademark Office*